(12) United States Patent
Chattaway et al.

(10) Patent No.: US 11,324,982 B1
(45) Date of Patent: May 10, 2022

(54) FIRE SUPPRESSION COMPOSITIONS

(71) Applicant: Kidde Technologies Inc., Wilson, NC (US)

(72) Inventors: Adam Chattaway, Windsor (GB); Terry Simpson, Wake Forest, NC (US); Mark P. Fazzio, Wilson, NC (US); Eli Baldwin, Knightdale, NC (US); Marios C. Soteriou, Middletown, CT (US); Paul Papas, West Hartford, CT (US); Qing Liu, Wake Forest, NC (US)

(73) Assignee: KIDDE TECHNOLOGIES, INC., Wilson, NC (US)

( * ) Notice: Subject to any disclaimer, the term of this patent is extended or adjusted under 35 U.S.C. 154(b) by 0 days.

(21) Appl. No.: 17/073,515

(22) Filed: Oct. 19, 2020

(51) Int. Cl.
*A62D 1/00* (2006.01)
*C01B 32/50* (2017.01)
*C07C 19/16* (2006.01)

(52) U.S. Cl.
CPC .......... *A62D 1/0092* (2013.01); *C01B 32/50* (2017.08); *C07C 19/16* (2013.01)

(58) Field of Classification Search
None
See application file for complete search history.

(56) References Cited

U.S. PATENT DOCUMENTS

| | | | | |
|---|---|---|---|---|
| 5,611,210 A * | 3/1997 | Nimitz | ................... | C09K 5/044 62/114 |
| 8,920,668 B2 | 12/2014 | Mitchell et al. | | |
| 9,034,202 B2 | 5/2015 | Mitchell et al. | | |
| 9,713,732 B2 * | 7/2017 | Mitchell | ................... | A62D 1/00 |
| 10,953,257 B2 * | 3/2021 | Simpson | .............. | A62D 1/0057 |
| 2005/0145820 A1 * | 7/2005 | Waldrop | .............. | A62D 1/0092 252/3 |
| 2009/0109604 A1 * | 4/2009 | Yanabu | ................ | H02B 13/055 361/618 |
| 2012/0145941 A1 * | 6/2012 | Gibson | ................... | A62D 1/005 252/3 |
| 2013/0240217 A1 * | 9/2013 | Mitchell | ................... | A62D 1/00 169/5 |
| 2013/0240218 A1 * | 9/2013 | Mitchell | ................... | A62D 1/00 169/16 |
| 2015/0041157 A1 * | 2/2015 | Mitchell | ............ | A62C 99/0018 169/16 |
| 2019/0161660 A1 * | 5/2019 | Yana Motta | ............ | F25B 9/006 |
| 2019/0290950 A1 | 9/2019 | Hagge et al. | | |
| 2020/0094089 A1 | 3/2020 | Hagge et al. | | |
| 2020/0248933 A1 | 8/2020 | Mackin | | |
| 2020/0283666 A1 * | 9/2020 | Aydin | ..................... | C09K 5/045 |
| 2020/0330808 A1 * | 10/2020 | Simpson | .............. | A62D 1/0057 |
| 2020/0333233 A1 * | 10/2020 | Simpson | ................ | G01N 15/06 |

FOREIGN PATENT DOCUMENTS

| | | |
|---|---|---|
| CN | 106281232 A | 1/2017 |
| KR | 20010038267 A | 5/2001 |
| WO | 2019099961 A1 | 5/2019 |
| WO | 2021230935 A2 | 11/2021 |

OTHER PUBLICATIONS

Abstract for CN106281232 (A), Published: Jan. 4, 2017, 1 page.
Abstract for KR20010038267 (A), Publication: May 15, 2001, 1 page.
European Search Report for Application No. 21203496.1, dated Mar. 22, 2022, 3 pages.

\* cited by examiner

*Primary Examiner* — Joseph D Anthony
(74) *Attorney, Agent, or Firm* — Cantor Colburn LLP

(57) ABSTRACT

A fire suppression composition comprises $CF_3I$ and $CO_2$, wherein said $CF_3I$ is present in an amount of from 23 mol. % to 39 mol. %, based on the total moles of $CF_3I$ and $CO_2$ present in the fire suppression composition. Alternatively, the fire suppression composition comprises $CF_3I$ and $CO_2$, wherein said $CF_3I$ is present in an amount of from 53 mol. % to 85 mol. %, based on the total moles of $CF_3I$ and $CO_2$ present in the fire suppression composition.

9 Claims, No Drawings

FIRE SUPPRESSION COMPOSITIONS

TECHNICAL FIELD

The present disclosure relates to fire suppression compositions comprising $CF_3I$ and $CO_2$.

BACKGROUND

Halon 1301 has frequently been employed as a fire suppression agent. However, production of this agent was banned in 1994 due to its high ozone depleting potential. There is therefore a desire to replace Halon 1301 with more environmentally friendly fire suppression agents. A promising alternative to Halon 1301, $CF_3I$ (trifluoroiodomethane), failed a key MPS test, the bulk load test, and can be subject to decomposition during use. A solution must be found that will improve the stability of the alternative fire suppression agents.

SUMMARY

This disclosure relates to fire suppression compositions comprising blends of $CF_3I$ and $CO_2$. The $CF_3I$ is present in an amount of from 23 mol. % to 80 mol. %, based on the total amount of $CF_3I$ and $CO_2$ present in the fire suppression composition.

In one aspect, the present disclosure provides a fire suppression composition comprising $CF_3I$ and $CO_2$, wherein said $CF_3I$ is present in an amount of between 23 mol. % and 40 mol. %, e.g. from 23 mol. % to 39%, based on the total moles of $CF_3I$ and $CO_2$ present in the fire suppression composition.

The $CF_3I$ may be present in an amount of from 24 mol. % to 38 mol. %, e.g. from 25 mol. % to 37 mol. %, from 26 mol. % to 36 mol. %, from 27 mol. % to 35 mol. %, or from 28 mol. % to 34 mol. %, based on the total moles of $CF_3I$ and $CO_2$ present in the fire suppression composition.

The $CF_3I$ may present in an amount greater than 29 mol. % based on the total moles of $CF_3I$ and $CO_2$ present in the fire suppression composition, e.g. from 29 to 39 mol. %, 29 to 38 mol. %, 30 to 37 mol. %, 31 to 36 mol. %, 32 to 35 mol. %, or from 33 to 34 mol. %, based on the total moles of $CF_3I$ and $CO_2$ present in the fire suppression composition.

The $CF_3I$ may be present in an amount of from 23 mol. % to 39.9 mol. %, for example from 24.5 mol. % to 39.5 mol. %, from 25.5 mol. % to 39 mol. %, or from 30 mol. % to 38 mol. %, based on the total moles of $CF_3I$ and $CO_2$ present in the fire suppression composition.

The $CF_3I$ may be present in an amount of 22.5 mol. %, 23.5 mol. %, 25.3 mol. %, 25.5 mol. %, 30.4 mol. %, 30.5 mol. %, 32.4 mol. %, 32.5 mol. %, 35.1 mol. %, 35.5 mol. %, 39.9 mol. % or any ranges between any of these values, based on the total moles of $CF_3I$ and $CO_2$ present in the fire suppression composition. The $CF_3I$ may be present in an amount of 30 to 35 mol. %, based on the total moles of $CF_3I$ and $CO_2$ present in the fire suppression composition.

In a further aspect of the present disclosure, there is provided a fire suppression composition comprising $CF_3I$ and $CO_2$, wherein said $CF_3I$ is present in an amount greater than 53 mol. %, based on the total moles of $CF_3I$ and $CO_2$ present in the fire suppression composition.

The $CF_3I$ may be present in an amount of from 53 mol. % to 85 mol. %, e.g. 53 mol. % to 75 mol. %, based on the total moles of $CF_3I$ and $CO_2$ present in the fire suppression composition.

The $CF_3I$ may be present in an amount from 53 to 84 mol. %, 54 mol. % to 80 mol. %, 55 mol. % to 79 mol. %, 56 to 78 mol. %, 58 to 76 mol. %, 59 to 75 mol. %, 60 to 72 mol. %, 62 to 70 mol. %, 63 to 69 mol. %, 64 to 68 mol. %, or 65 to 67 mol. %, based on the total moles of $CF_3I$ and $CO_2$ present in the fire suppression composition.

The $CF_3I$ may be present in an amount of 67.2, 67.5, 75.5, 75.7, 80.1, 80.5, 83.3, 83.5 mol. % or any ranges between any of these values, based on the total moles of $CF_3I$ and $CO_2$ present in the fire suppression composition. The $CF_3I$ may be present in an amount of 67 to 80 mol. %, based on the total moles of $CF_3I$ and $CO_2$ present in the fire suppression composition.

The amount of $CF_3I$, expressed as a percentage of the total amount of $CF_3I$ and $CO_2$ in the fire suppression composition, may also be expressed in weight %.

Thus, in a further aspect of the present disclosure, there is provided a fire suppression composition comprising $CF_3I$ and $CO_2$, wherein said $CF_3I$ is present in an amount of between 57 weight % and 75 weight %, e.g. from 57 weight % to 74 weight %, based on the total weight of $CF_3I$ and $CO_2$ present in the fire suppression composition.

The $CF_3I$ may be present in an amount of from 57 weight % to 74 weight %, for example from 58 to 73 weight %, from 60 to 72 weight %, from 61 to 71 weight %, from 62 to 70 weight %, or from 63 to 69 weight %, based on the total weight of $CF_3I$ and $CO_2$ present in the fire suppression composition.

The $CF_3I$ may be present in an amount of greater than 65 weight %, e.g. 65 to 74 weight %, from 65 to 73 weight %, 66 to 72 weight %, 67 to 71 weight %, from 68 to 70 weight %, or from 69 to 70 weight %, based on the total weight of $CF_3I$ and $CO_2$ present in the fire suppression composition.

The $CF_3I$ may be present in an amount of from 57 weight % to 74.7 weight %, for example from 59 weight % to 74.4 weight %, from 60.3 weight % to 74 weight %, or from 65 weight % to 73 weight %, based on the total weight of $CF_3I$ and $CO_2$ present in the fire suppression composition.

The $CF_3I$ may be present in an amount of 56.4 weight %, 57.8 weight %, 60.1 weight %, 60.3 weight %, 66 weight %, 66.1 weight %, 68.1 weight %, 68.2 weight %, 70.7 weight %, 71 weight %, 74.7 weight % or any ranges between any of these values, based on the total weight of $CF_3I$ and $CO_2$ present in the fire suppression composition.

In a further aspect of the present disclosure, there is provided a fire suppression composition comprising $CF_3I$ and $CO_2$, wherein the $CF_3I$ is present in an amount of greater than 83 weight %, for example from 83 weight % to 96 weight %, e.g. 83 weight % to 93 weight %, based on the total weight of $CF_3I$ and $CO_2$ present in the fire suppression composition.

The $CF_3I$ may be present in an amount of from 83 to 96 weight %, 84 weight % to 95 weight %, 84 weight % to 94 weight %, 85 weight % to 94 weight %, 86 to 93 weight %, 87 to 92 weight %, 87 to 91 weight %, 87 to 90 weight %, 88 to 90 weight %, 89 to 90 weight %, or 90 to 91 weight % based on the total weight of $CF_3I$ and $CO_2$ present in the fire suppression composition.

In one aspect of the disclosed compositions, $CF_3I$ is present in an amount of 90.1, 90.2, 93.2, 93.3, 94.7, 94.8, 95.7, 95.7 weight %, or any ranges between any of these values, based on the total weight of $CF_3I$ and $CO_2$ present in the fire suppression composition.

As the amount of $CF_3I$ is expressed as proportion of the total of $CF_3I$ and $CO_2$, it will be understood that the percentage of $CO_2$ (also expressed as a proportion of the total) is the remainder of this total (i.e. 100 minus the percentage of $CF_3I$). Where the composition consists of, or consists essentially of, $CF_3I$ and $CO_2$, these proportions will also be applicable to the composition as a whole. Fire suppression compositions comprising such blends of $CF_3I$ and $CO_2$, e.g. those with molar ratios of $CF_3I$ to $CO_2$ of from 3:7 to 7:13, or 2:1 to 5:1 forma further aspect of this disclosure.

In addition to $CF_3I$ and $CO_2$, the fire suppression composition as disclosed herein can further comprise one or more additional components. The additional components may be selected from a gas (e.g. an inert gas), an additional fire suppressant compound, odorants, or combinations thereof.

The total amount of additional components, if present, may be present in an amount of up to 20 weight %, based on the total weight of the fire suppression composition.

The total amount of additional components present in the fire suppression composition may be up to 18 weight %, up to 15 weight %, up to 10 weight %, up to 8 weight %, up to 5 weight % or up to 3 weight %, (e.g. from 0.1 weight % up to these limits) based on the total weight of the fire suppression composition. In some aspects, the total amount of additional components present in the fire suppression composition may be up to 2 weight % or up to 1 weight %, e.g. 0.1 weight % to 2 weight % or 0.1 weight % to 1 weight %.

The additional components, if present, may be one or more gases, e.g. an inert gas, or a propellant. Examples of suitable gases include nitrogen, argon, helium and neon, and combinations thereof.

The optional gas may be present in an amount of up to 1 weight %, based on the total weight of the fire suppression composition. For example, the gas may be present in an amount of up to 0.9 weight %, up to 0.8 weight %, up to 0.7 weight %, up to 0.6 weight %, up to 0.5 weight %, up to 0.4 weight %, up to 0.3 weight %, up to 0.2 weight % or up to 0.1 weight %, based on the total weight of the fire suppression composition. If present, a lower limit for the gas may be 0.05 weight %.

The additional component, if present, may be an additional fire suppressant compound, i.e. one that is not $CF_3I$ or $CO_2$.

The additional fire suppressant compound, if present, may be present in an amount of up to 20 weight %, based on the total weight of the fire suppression composition. For example, the total amount of additional fire suppressant compound present in the fire suppression composition may be up to 18 weight %, up to 15 weight %, up to 10 weight %, up to 8 weight %, up to 5 weight % or up to 3 weight % based on the total weight of the fire suppression composition. If present, a lower limit for the additional suppressant may be 0.1 weight %.

The additional component, if present, can be an odorant. Examples of odorants include compounds which include one or more carbon-carbon double bonds, and/or compounds which are aromatic. The odorant compounds may further include a hydroxyl group, an iodine group, or both.

The odorant compound, if present, may be present in an amount of up to 1 weight % based on the total weight of the fire suppression composition. For example, the odorant may be present in an amount of up to 0.9 weight %, up to 0.8 weight %, up to 0.7 weight %, up to 0.6 weight %, up to 0.5 weight %, up to 0.4 weight %, up to 0.3 weight %, up to 0.2 weight % or up to 0.1 weight %, based on the total weight of the fire suppression composition. If present, a lower limit for the odorant may be 0.05 weight %.

The present disclosure also provides a device, e.g. a fire extinguisher, fire suppression device, or storage device, comprising a fire suppression composition as herein described.

Also disclosed is a device, e.g. a fire extinguisher, fire suppression device, or storage device, comprising at least two separate containers, wherein the first container comprises $CF_3I$ and the second container comprises $CO_2$. The proportions of the $CF_3I$ and the $CO_2$ are as described herein. The contents of the containers can be combined immediately prior to use to produce a fire suppression composition as herein described. As would be understood, the first and/or second container can comprise one or more additional components (e.g. one or more additional components as herein described) or any additional components can be stored in a further container or containers.

Disclosed is a fire suppression system or device comprising a fire suppression composition as herein described, or the components thereof. The fire suppression system can comprise a fire suppression composition herein described and a dispensing component (such as one or more nozzles that disperse the fire suppression composition). In an alternative aspect, the fire suppression system can contain: (i) two separate containers, wherein the first container comprises $CF_3I$ and the second container comprises $CO_2$, and (ii) a combining and dispensing component which is configured to combine the contents of the separate containers to form a fire suppression composition as herein described, and then dispense said resulting fire suppression composition.

Also disclosed is a method for extinguishing a fire comprising using a fire suppression composition as herein described.

Disclosed is a method for preparing a fire suppression composition as herein described, said method comprising combining $CF_3I$ and $CO_2$ such that $CF_3I$ is present in an amount as herein described in relation to the total amount of $CF_3I$ and $CO_2$. The method may comprise the steps of (i) providing $CF_3I$, (ii) providing $CO_2$ and (iii) combining $CF_3I$ and $CO_2$ such that $CF_3I$ is present in an amount as herein described in relation to the total amount of $CF_3I$ and $CO_2$. The method can further comprise the additional step of adding one or more additional components as herein described.

In some aspects, the fire suppression composition of the present disclosure consists of, or consists essentially of, $CF_3I$ and $CO_2$ in the proportions described herein.

DETAILED DESCRIPTION $CF_3I$ is an environmentally friendly alternative to fire suppression agents like Halon 1301 because $CF_3I$ has a lower ozone depletion potential. The lower ozone depletion potential is due to the lower stability of the molecule. However, the lower stability (or the increased tendency to degrade) presents a challenge for storage and use of $CF_3I$ or blends containing $CF_3I$ as a fire suppression agent. The lower stability has discouraged the use of $CF_3I$ in fire suppression applications as it can decompose, thus reducing its efficacy. The present disclosure involves addition of $CO_2$ to the $CF_3I$, which has been found to improve stability of $CF_3I$.

When released, the $CO_2$ is able to remove a large amount of heat from its surroundings (i.e. has a high latent heat of vaporization). This temperature reduction can reduce the severity of the fire, as well as reducing the decomposition rate of $CF_3I$, maximizing the available $CF_3I$ present when the fire suppression composition is used to extinguish a fire.

The presence of $CO_2$ in the fire suppression composition can reduce the temperature of the atmosphere in the space to be protected to below 370° C. (700° F.), e.g. to below 360° C., to below 350° C., to below 340° C., to below 330° C., to below 320° C., or to below 315° C. (600° F.).

$CO_2$ is a physically acting fire suppression agent and $CF_3I$ is a chemically acting agent. Combining these two different types of agent as described herein results in a synergistic combination. More specifically, the blends of $CO_2$ and $CF_3I$ as disclosed herein have been shown to be a synergistic combination. The combination of these two components has surprisingly resulted in a fractional inerting composition number of less than the sum of the two components when measured separately. The effect of this is that the combination of these two components has an enhanced ability to extinguish a fire than the two components would have had if used separately in the same amount.

It has also been found that fire suppression compositions according to the present disclosure can have a reduced vapor pressure, and in some instances, a vapor pressure in the same range as that of conventional fire suppression agents such as Halon 1301. The reduced vapor pressure allows the fire suppression composition to be used in conventional hardware such as preexisting fire extinguishing containers and devices.

The present disclosure will now be further described by way of the following non-limiting examples.

EXAMPLES

Testing Procedure

Testing was carried out against propane-air explosions in a 42 L sphere. The most explosive propane-air mixture is 4% propane in air. This concentration was therefore used to assess the relative performance of extinguishing agents and blends thereof.

The sphere was evacuated. Whilst monitoring the pressure transducer, propane was added to a pressure of 0.04 atm (4% in the final mix). The agent or agents were added at the desired concentration. Air was then added to raise the pressure in the sphere to 1.00 atm. A fan can then be used to ensure that all the gases are mixed homogeneously throughout the sphere. A spark was ignited using a center point spark ignition and the pressure rise was monitored by a data logger. A pressure rise of 1 psi or lower is designated as a pass.

The standards used for inerting testing are:
ASTM E2079-07—the standard test method for limiting oxidant concentration in gases and vapors
BS EN 1839:2012—determination of explosion limits in gases and vapors
BS EN 15967:2012—determination of maximum explosion pressure and the maximum rate of pressure rise of gases and vapors.

Fractional Inerting Contribution

When assessing blends of components, the concept of fractional inerting contribution is used. This is defined as:

$$FIC = \sum_{i=1}^{n} \frac{C_i}{IC_i}$$

Where $C_i$ is the concentration of component i.
And $IC_i$ is the inerting concentration of component i.
Thus, inerting should be attained when FIC=1 (i.e. the sum of individual concentrations has reached the overall required amount to achieve inerting). It therefore follows that if inerting is achieved at FIC less than 1, then the blend is more effective than the sum of its components. In other words, the blend is exhibiting synergy.

Blends of $CF_3I$ and $CO_2$

Blends of $CF_3I$ and $CO_2$ were evaluated and it was found that successful inerting results were found at FIC values of lower than 1:

TABLE I

| Example | Propane (Vol %) | $CF_3I$ (Vol %) | $CO_2$ (Vol %) | Mol Ratio | Pres rise (psig) | FIC | Rel. wt to 6% Halon 1301 | Rel. vol to 6% Halon 1301 | Mol. % $CF_3I$* |
|---|---|---|---|---|---|---|---|---|---|
| 1 | 3.98 | 2.93 | 8.64 | 1:3 | 0.99 | 0.76 | 1.04 | 1.36 | 25.3 |
| 2 | 4.01 | 3.24 | 7.42 | 3:7 | 0.91 | 0.76 | 1.04 | 1.27 | 30.4 |
| 3 | 4.02 | 3.31 | 6.92 | 6:13 | 0.78 | 0.76 | 1.03 | 1.22 | 32.4 |
| 4 | 4.05 | 3.49 | 6.46 | 7:13 | 0.9 | 0.77 | 1.04 | 1.2 | 35.1 |

*Mol. % $CF_3I$ expressed as a proportion of the moles of $CF_3I$ and $CO_2$

TABLE II

| Example | Propane (Vol %) | $CF_3I$ (Vol %) | $CO_2$ (Vol %) | Mol Ratio | Pres rise (psig) | FIC | Rel. wt to 6% Halon 1301 | Rel. vol to 6% Halon 1301 | Mol. % $CF_3I$* |
|---|---|---|---|---|---|---|---|---|---|
| 5 | 4.04 | 5.19 | 2.53 | 2:1 | 0.94 | 0.89 | 1.22 | 1.06 | 67.2 |
| 6 | 3.98 | 5.47 | 1.76 | 3:1 | 0.97 | 0.90 | 1.25 | 1.03 | 75.7 |
| 7 | 4.08 | 6.01 | 1.49 | 4:1 | 0.97 | 0.98 | 1.36 | 1.09 | 80.1 |
| 8 | 4.01 | 6.49 | 1.3 | 5:1 | 0.96 | 1.04 | 1.46 | 1.15 | 83.3 |

*Mol. % $CF_3I$ expressed as a proportion of the moles of $CF_3I$ and $CO_2$

As can be seen from Tables I and II above, all examples show a synergistic effect between the $CF_3I$ and $CO_2$ in the blend. Examples 1~4 show a particularly good synergistic effect, coupled with an acceptable vapor pressure/temperature characteristics. Examples 5-8 show a synergistic effect, and these examples have improved vapor pressure/temperature characteristics.

References to "comprises" and/or "comprising," should be understood to also encompass "consist(s) of", "consisting of", "consist(s) essentially of" and "consisting essentially of".

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

The invention claimed is:

1. A fire suppression composition comprising $CF_3I$ and $CO_2$, wherein said $CF_3I$ is present in an amount of from 23 mol. % to 39 mol. %, based on the total moles of $CF_3I$ and $CO_2$ present in the fire suppression composition;
   wherein a total amount of additional components present in the fire suppression composition is in an amount of up to 20 weight %, based on the total weight of the fire suppression composition.

2. The fire suppression composition according to claim 1, wherein said $CF_3I$ is present in an amount of from 29 mol. % to 39 mol. %, based on the total moles of $CF_3I$ and $CO_2$ present in the fire suppression composition.

3. The fire suppression composition according to claim 1, wherein said $CF_3I$ is present in an amount of from 30 mol. % to 35 mol. %, based on the total moles of $CF_3I$ and $CO_2$ present in the fire suppression composition.

4. The fire suppression composition according to claim 1, wherein the additional components are selected from one or more gases, additional fire suppressant compounds, odorants, or combinations thereof.

5. The fire suppression composition according to claim 1, wherein the total amount of additional components are present in an amount of up to 5 weight %, based on the total weight of the fire suppression composition.

6. A fire suppression system or device containing the fire suppression composition as claimed in claim 1.

7. A fire suppression system or device according to claim 6, wherein said fire suppression system additionally comprises a dispensing component.

8. A method for preparing a fire suppression composition as claimed in claim 1, said method comprising the steps of (i) providing $CF_3I$, (ii) providing $CO_2$ and (iii) combining $CF_3I$ and $CO_2$ to form a fire suppression composition as defined in claim 1.

9. A method for preparing a fire suppression composition as claimed in claim 1, said method comprising the steps of (i) providing $CF_3I$, (ii) providing $CO_2$ and (iii) combining $CF_3I$ and $CO_2$ to form a fire suppression composition as defined in claim 1.

\* \* \* \* \*